(12) United States Patent
Baek

(10) Patent No.: US 12,029,871 B1
(45) Date of Patent: Jul. 9, 2024

(54) NASAL CATHETER WITH GUIDE WALL

(71) Applicant: Young Jin Baek, Changwon-si (KR)

(72) Inventor: Young Jin Baek, Changwon-si (KR)

( * ) Notice: Subject to any disclaimer, the term of this patent is extended or adjusted under 35 U.S.C. 154(b) by 0 days.

(21) Appl. No.: 18/440,996

(22) Filed: Feb. 14, 2024

(30) Foreign Application Priority Data

Mar. 9, 2023 (KR) .................. 10-2023-0031266

(51) Int. Cl.
*A61M 3/02* (2006.01)

(52) U.S. Cl.
CPC ....... *A61M 3/0279* (2013.01); *A61M 2205/60* (2013.01); *A61M 2210/0618* (2013.01)

(58) Field of Classification Search
CPC ........ A61M 3/0279; A61M 2210/0618; A61M 3/0275; A61C 5/44
See application file for complete search history.

(56) References Cited

U.S. PATENT DOCUMENTS

2017/0119953 A1* 5/2017 Wen ..................... A61M 11/007

FOREIGN PATENT DOCUMENTS

| CN | 103800973 A | 5/2014 |
|---|---|---|
| JP | 2003-310706 A | 11/2003 |
| JP | 2008-295849 A | 12/2008 |
| JP | 6586004 B2 | 10/2019 |
| KR | 20-0481301 Y1 | 9/2016 |
| KR | 10-2022-0097884 A | 7/2022 |

* cited by examiner

*Primary Examiner* — Deanna K Hall
(74) *Attorney, Agent, or Firm* — Revolution IP, PLLC

(57) ABSTRACT

The present invention relates to a nasal catheter with a guide wall, and more particularly, to a nasal catheter with a guide wall, the nasal catheter including a tube main body which is connected to one end of each shaft of a device spraying a medicinal fluid or irrigation fluid and an aspiration device performing aspiration inside a nasal cavity and which is inserted into the nasal cavity and a guide wall portion which is configured to form a slope at one side of an inner portion of a front end portion of the tube main body to allow the medicinal fluid or irrigation fluid to be sprayed in an eccentric direction.

2 Claims, 4 Drawing Sheets

NASAL CATHETER WITH GUIDE WALL

CROSS-REFERENCE TO RELATED APPLICATION

This application claims priority to and the benefit of Korean Patent Application No. 10-2023-0031266, filed on Mar. 9, 2023, the disclosure of which is incorporated herein by reference in its entirety.

BACKGROUND

1. Field of the Invention

The present invention relates to a nasal catheter with a guide wall, and more particularly, to a nasal catheter with a guide wall in which a guide wall portion is formed at one side of an inner portion of a front end portion of a tube main body to allow a medicinal fluid or irrigation fluid to be sprayed in a direction parallel to a nasal meatus and reduce pressure applied to a nasal septum.

2. Discussion of Related Art

Generally, nasal catheters are connected to one end of a shaft coupled to a nasal irrigator to spray a medicinal fluid or irrigation fluid and are used to wash off, disinfect, or suction purulent mucus or solidified secretion caused by an inflammation of the inside of the nose, such as a nasal cavity or paranasal cavity, through a pump.

Here, the nasal cavity is an empty space inside the nose, and a mucous membrane having fine hair vibrating only in one direction formed thereon is formed inside the nasal cavity. The surface of the fine hair is coated with mucus which filters harmful substances such as dust, viruses, and pollen contained in the air. Also, since the substances filtered by the mucous membrane move from the nose to the stomach through the throat together with the mucus, only purified air is delivered to lungs.

Nowadays, due to industrial development and urbanization, modern people inhale polluted air containing smoke from numerous vehicles and industrial wastes generated in industrial sites and harmful air containing house dust, mite, pollen, animal hair, which may cause allergies, and various viruses such as coronavirus, adenovirus, rhinovirus, and influenza virus contained in the air that are the main causes of cold.

The inhaled harmful air continuously stimulates the mucous membrane inside the nasal cavity, degrades functions and the normal defense mechanism of the mucous membrane, and causes inflammatory rhinitis. Also, when the harmful air contains harmful viruses, the harmful air may cause respiratory diseases.

Accordingly, in medical institutions where respiratory diseases are treated, a nasal catheter is used by being connected to a nasal irrigator and a nasal aspirator in order to irrigate the nasal cavity and oral cavity with a drug and remove harmful substances adhered to the mucous membrane.

However, the nasal catheter of the related art has a problem in that, when the nasal catheter is inserted into a nasal cavity to spray a medicinal fluid or irrigation fluid, pressure is applied to a nasal septum, and bleeding occurs.

RELATED ART DOCUMENT

Patent Document (Patent Document 1) Korean Patent Registration No. 20-0481301 (Date of Registration: Sep. 9, 2016)

SUMMARY OF THE INVENTION

The present invention is directed to a nasal catheter with a guide wall having a new structure in which a guide wall portion is formed at one side of an inner portion of a front end portion of a tube main body to allow a medicinal fluid or irrigation fluid to be sprayed in a direction parallel to a nasal meatus and reduce pressure applied to a nasal septum.

The present invention is also directed to a nasal catheter with a guide wall that reduces pressure applied to a nasal septum even when a front end portion of a tube main body is positioned in the sine (sin) direction relative to the nasal septum.

The present invention is also directed to a nasal catheter with a guide wall in which an identifier is formed to determine the position of a guide wall portion formed at an inner side of a front end portion of a tube main body.

The present invention is also directed to a nasal catheter with a guide wall that reduces pressure applied to a nasal septum even when connected to a nasal aspiration device and performing aspiration with negative pressure.

According to an aspect of the present invention, there is provided a nasal catheter with a guide wall, the nasal catheter including: a tube main body connected to one end of a shaft of a device spraying a medicinal fluid or irrigation fluid and inserted into a nasal cavity; and a guide wall portion configured to form a slope at one side of an inner portion of a front end portion of the tube main body to allow the medicinal fluid or irrigation fluid to be sprayed in an eccentric direction.

In the nasal catheter, the guide wall portion may allow the medicinal fluid or irrigation fluid to be sprayed in a direction parallel to a nasal meatus when the tube main body is positioned in the sin direction relative to the nasal septum.

In the nasal catheter, the guide wall portion may have a cross-section formed in any one of a triangular shape in which one side has an upward slope toward the front end portion of the tube main body, a triangular shape with one concave side, a triangular shape with one convex side, and a quadrangular shape.

The nasal catheter may further include an identifier formed at an outer circumferential surface of a rear end portion of the tube main body corresponding to a straight line in a direction facing the guide wall portion and configured to determine the position of the guide wall portion.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF THE INVENTION

Figure 1:
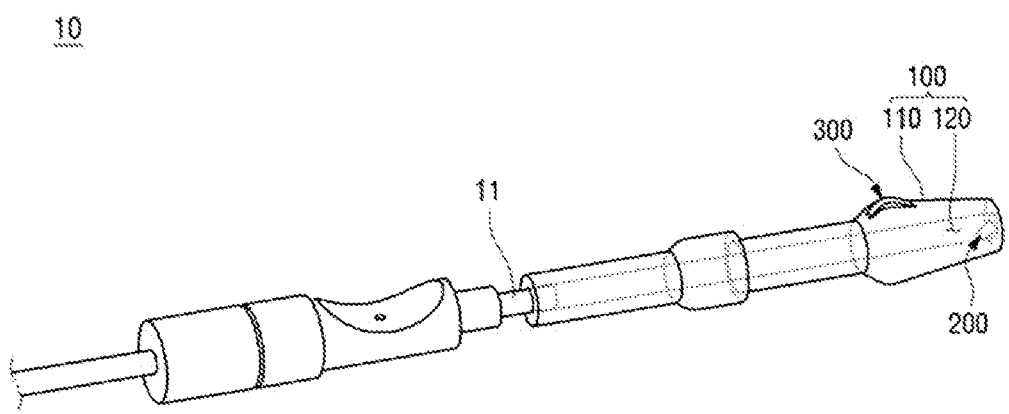
FIG. 1 is a perspective view illustrating an exterior of a nasal catheter with a guide wall according to an embodiment of the present invention.

Hereinafter, exemplary embodiments of the present invention will be described in detail with reference to the accompanying drawings to allow those of ordinary skill in the art to which the present invention pertains to easily practice the present invention. However, in describing the operation principles relating to the exemplary embodiments of the present invention in detail, when detailed description of a relevant known function or configuration is deemed as having the possibility of unnecessarily obscuring the gist of the present invention, the detailed description thereof will be omitted.

Also, throughout the drawings, parts performing similar functions and actions are denoted by the same reference numerals.

In addition, throughout the specification, when a certain part is described as being "connected" to another part, this not only includes a case in which the part is directly connected to the other part, but also includes a case in which the part and the other part are indirectly connected to each other with another component disposed therebetween. Also, when a certain part is described as "including" a certain component, unless particularly described otherwise, this means that the part may further include other components instead of excluding other components.

Hereinafter, a nasal catheter with a guide wall according to an exemplary embodiment of the present invention will be described in detail with reference to the accompanying drawings.

Figure 2:
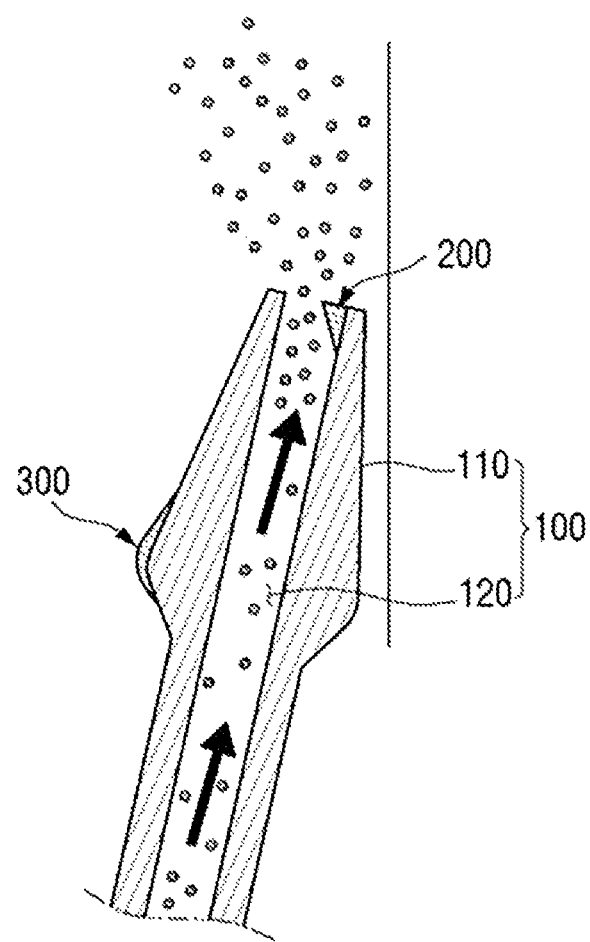
FIG. 2 is a cross-sectional view illustrating the nasal catheter with a guide wall according to an embodiment of the present invention.
Figure 3:
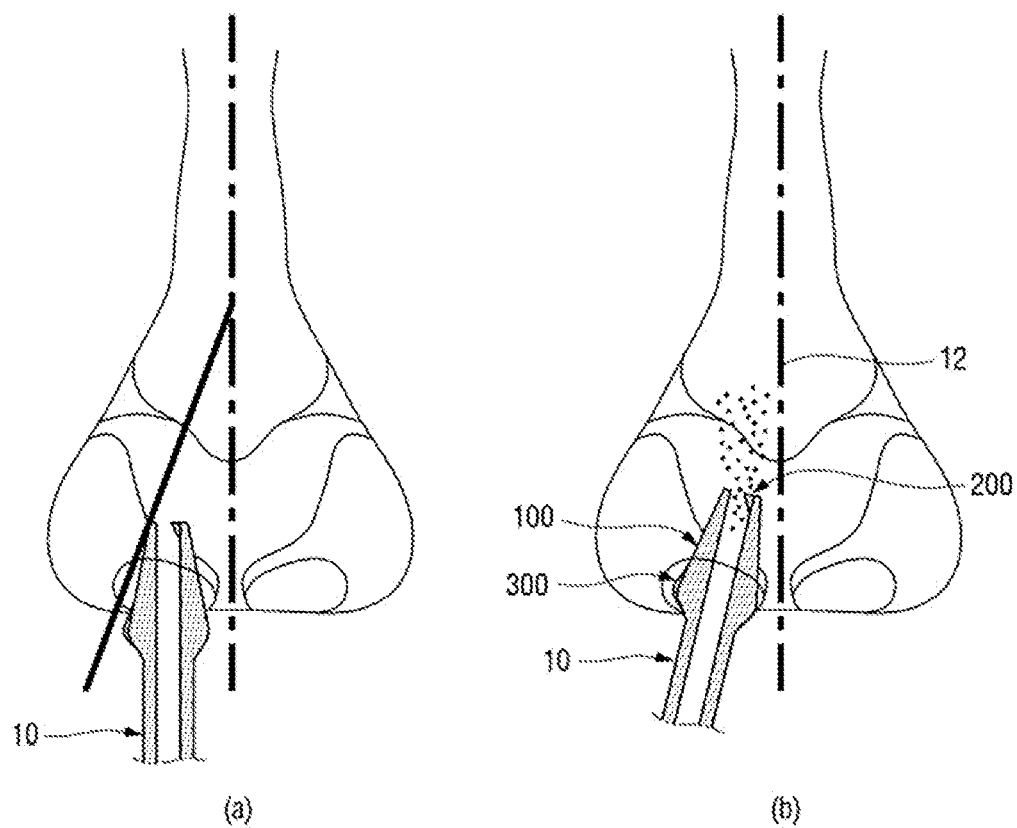
FIG. 3 is an exemplary view illustrating the concept of the nasal catheter with a guide wall according to an embodiment of the present invention.
Figure 4:
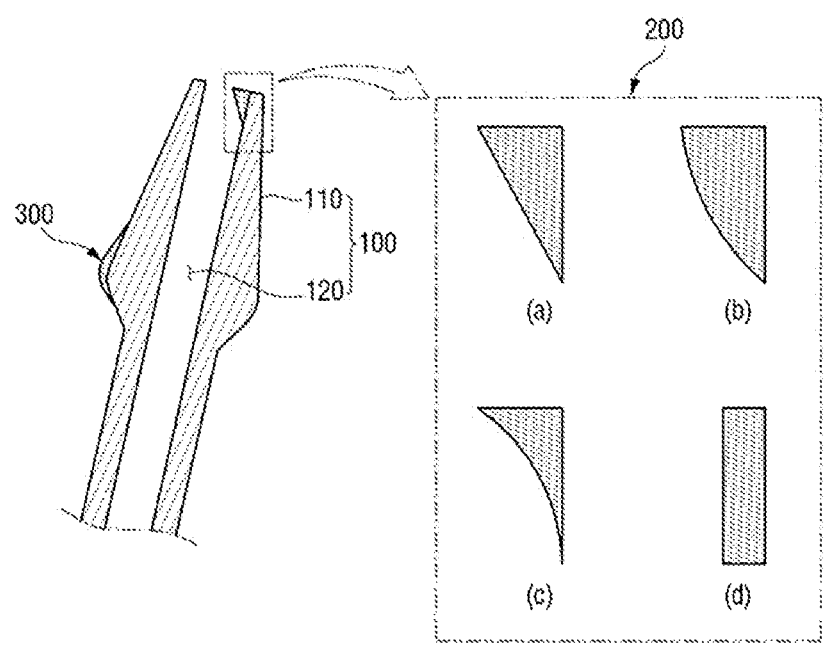
FIG. 4 is an exemplary view illustrating various shapes of a guide wall portion of the nasal catheter with a guide wall according to an embodiment of the present invention.

FIG. 1 is a perspective view illustrating an exterior of a nasal catheter with a guide wall according to an embodiment of the present invention, FIG. 2 is a cross-sectional view illustrating the nasal catheter with a guide wall according to an embodiment of the present invention, FIG. 3 is an exemplary view illustrating the concept of the nasal catheter with a guide wall according to an embodiment of the present invention, and FIG. 4 is an exemplary view illustrating various shapes of a guide wall portion of the nasal catheter with a guide wall according to an embodiment of the present invention.

As illustrated in FIG. 1, a nasal catheter 10 with a guide wall according to an embodiment of the present invention includes a tube main body 100 and a guide wall portion 200.

More specifically, as illustrated in FIGS. 1 and 2, the nasal catheter 10 with a guide wall according to an embodiment of the present invention includes the tube main body 100 connected to one end of a shaft 11 of a device spraying a medicinal fluid or irrigation fluid and inserted into a nasal cavity and the guide wall portion 200 configured to form a slope at one side of an inner portion of a front end portion of the tube main body to allow the medicinal fluid or irrigation fluid to be sprayed in an eccentric direction.

Also, the tube main body 100 of the nasal catheter 10 with a guide wall according to an embodiment of the present invention may be connected to one end of a shaft of a nasal aspiration device and perform aspiration of purulent mucus or solidified secretion caused by an inflammation and harmful substances inside the nasal cavity. Accordingly, the nasal catheter 10 with a guide wall according to an embodiment of the present invention may be connected to each of a device spraying a medicinal fluid or irrigation fluid and an aspiration device performing aspiration inside the nasal cavity or may be selectively connected to one of them.

Also, for convenience of description of technology of the present invention, description of spraying through a nasal spraying device may be referenced for detailed description of performing aspiration using a nasal aspiration device. Also, in the drawings of the present specification, illustration of the principle of aspiration is omitted because the principle of spraying may identically apply thereto.

Referring to FIGS. 1 and 2, the tube main body 100 is formed as a pipeline which has flexibility to be inserted into a nasal cavity and has both sides open. Also, the tube main body 100 is connected to one end of the shaft 11 connected to a device spraying a medicinal fluid or irrigation fluid.

The tube main body 100 further includes a conical portion 110 and a passage 120.

The conical portion 110 is formed as an extending portion which has a diameter gradually increasing from a front end portion to a rear end portion and is connected to one end of the shaft 11.

That is, the conical portion 110 has a shape in which a diameter is formed to be small at the front end portion for the front end portion to be inserted into the nasal cavity and increases toward the rear end portion to prevent the tube main body 100 from being excessively inserted into the nasal cavity. Also, the conical portion 110 may have a certain elastic force to maintain its shape inside the nasal cavity.

The passage 120 allows the front end portion, the rear end portion, and the extending portion of the conical portion 110 to communicate with each other and allows the medicinal fluid or irrigation fluid moved from the shaft 11 to be sprayed through the front end portion of the conical portion 110.

Referring to FIGS. 2 and 3, the guide wall portion 200 forms a slope at one side of an inner portion of the front end portion of the tube main body 100 to allow the medicinal fluid or irrigation fluid to be sprayed in an eccentric direction.

For example, since the nasal cavity has a structure that gradually narrows which is not suitable for a catheter to enter the nasal cavity, the tube main body 100 is not able to enter the nasal cavity as illustrated in FIG. 3A. Therefore, the tube main body 100 including the conical portion 110 having a narrowing front end portion is obliquely inserted into the nasal cavity as illustrated in FIG. 3B.

Here, in a case where a medicinal fluid or irrigation fluid is sprayed, a direction of aspiration and spraying is toward a nasal septum 12 with a typical catheter. The nasal septum 12 is prone to bleeding, and thus when pressure is applied thereto, nose bleeding may occur.

In order to address such a problem, the guide wall portion 200 is formed at an inner side of the passage 120 at the front end portion of the conical portion 110 in the present invention.

As illustrated in FIGS. 2 and 3B, the guide wall portion 200 serves to allow the medicinal fluid or irrigation fluid to be sprayed in a direction parallel to a nasal meatus when the tube main body 100 is positioned in the sine (sin) direction relative to the nasal septum 12.

For example, in order to irrigate the nasal cavity, the tube main body 100 of the present invention may be inserted into the nasal cavity to be positioned in the sin direction relative to the nasal septum 12. Also, the medicinal fluid or irrigation fluid is introduced into the passage 120 through the shaft 11 and sprayed through the front end portion of the conical portion 110.

Here, since the medicinal fluid or irrigation fluid is discharged and sprayed in an eccentric direction due to the guide wall portion 200 as illustrated in FIG. 3B, the medicinal fluid or irrigation fluid moves in a direction parallel to a nasal meatus forming the inside of the nasal cavity. As a result, pressure applied to the nasal septum 12 is decreased, and thus tissue damage is reduced, and occurrence of bleeding can be prevented.

Also, not only when the medicinal fluid or irrigation fluid is sprayed, but also when aspiration of purulent mucus or solidified secretion caused by an inflammation and harmful substances introduced into the nasal cavity is performed, the aspiration is performed in the direction parallel to the nasal meatus, and thus, damage to the nasal septum 12 can be prevented.

Also, as illustrated in FIG. 4, in the nasal catheter 10 with a guide wall according to an embodiment of the present invention, the guide wall portion 200 may have a cross-section formed in any one of a triangular shape in which one side has an upward slope toward the front end portion of the tube main body 100, a triangular shape with one concave side, a triangular shape with one convex side, and a quadrangular shape.

That is, when the medicinal fluid or irrigation fluid moving along the inside of the passage 120 is sprayed through the front end portion of the conical portion 110, the guide wall portion 200 is formed in any of the above-listed shapes in a space that corresponds to a radius of the passage 120 so that the medicinal fluid or irrigation fluid is discharged in an eccentric direction. As a result, due to the medicinal fluid or irrigation fluid being sprayed in the direction parallel to the nasal meatus as described above, pressure applied to the nasal septum 12 can be reduced.

Meanwhile, as illustrated in FIGS. 1 and 2, the nasal catheter 10 with a guide wall according to an embodiment of the present invention may further include an identifier 300.

The identifier 300 is formed at an outer circumferential surface of a rear end portion of the tube main body 100 corresponding to a straight line in a direction facing the guide wall portion 200 and serves to determine the position of the guide wall portion 200.

For example, when the tube main body 100 is inserted into the nasal cavity, there is an inconvenience of having to check the part where the guide wall portion 200 is formed to make sure that the front end portion of the conical portion 110 at which the guide wall portion 200 is formed is positioned at the nasal septum 12. In order to eliminate such an inconvenience, the identifier 300 may be checked, and then the front end portion of the conical portion 110 may be inserted into the nasal cavity.

Here, the identifier 300 may be formed to protrude from an outer circumferential surface of a rear end portion of the conical portion 110 or may be expressed with a different color from the conical portion 110 to be distinguished therefrom. Also, the identifier 300 may be further formed at an outer circumferential surface of an extending portion that is made of the passage 120 extending from the rear end portion of the conical portion 110.

A nasal catheter with a guide wall according to the present invention has a guide wall portion formed at one side of an inner portion of a front end portion of a tube main body, thereby allowing a medicinal fluid or irrigation fluid to be sprayed in a direction parallel to a nasal meatus and reducing pressure applied to a nasal septum. In this way, there is an advantage in that bleeding of the nasal septum is prevented.

Also, even when the front end portion of the tube main body is positioned in the sin direction relative to the nasal septum due to the structure of the nasal cavity, pressure applied to the nasal septum can be reduced because the medicinal fluid or irrigation fluid is sprayed by passing through the guide wall portion.

Also, the nasal catheter with a guide wall according to the present invention has an identifier formed at an outer circumferential surface of a rear end portion of the tube main body to determine the position of the guide wall portion formed at an inner side of the front end portion of the tube main body. As a result, when the tube main body is inserted into the nasal cavity, an inconvenience of having to check the position of the guide wall portion can be reduced.

In addition, the nasal catheter with a guide wall according to the present invention can reduce pressure applied to the nasal septum even when connected to a nasal aspiration device and performing aspiration of nasal discharge with negative pressure instead of spraying the medicinal fluid or irrigation fluid.

Exemplary embodiments of the present invention have been described above in the detailed description of the present invention, but the embodiments are only illustrative and not intended to limit the present invention. Also, of course, those of ordinary skill in the art to which the present invention pertains may make various modifications within the scope not departing from the scope of the technical spirit of the present invention.

Therefore, the scope of rights of the present invention is not limited to the embodiments described above and may be implemented using various embodiments within the scope of the appended claims. Also, various modifications that may be made by those of ordinary skill in the art to which the invention pertains without departing from the gist of the present invention claimed in the claims also belong to the scope of the claims of the present invention.

The invention claimed is:

1. A nasal catheter with a guide wall, the nasal catheter comprising:
   a tube main body (100) including a conical portion (110), which is formed as an extending portion which has a diameter gradually increasing from a front end portion to a rear end portion and is connected to one end of a shaft (11) of a device spraying a medicinal fluid or irrigation fluid, and inserted into a nasal cavity;
   a guide wall portion (200) configured to form a slope at one side of an inner portion of the front end portion of the tube main body (100) to allow the medicinal fluid or irrigation fluid to be sprayed in an eccentric direction; and
   an identifier (300) protruding from an outer circumferential surface of the rear end portion of the tube main body (100) in a direction corresponding to a straight line facing the guide wall portion (200), and having a color distinguishable from the conical portion (110) to determine the position of the guide wall portion (200),
   wherein the guide wall portion (200) allows the medicinal fluid or irrigation fluid to be sprayed in a direction parallel to a nasal meatus when the tube main body (100) is positioned in a sine (sin) direction relative to a nasal septum.

2. The nasal catheter of claim 1, wherein the guide wall portion (200) has a cross-section formed in any one of a triangular shape in which one side has an upward slope toward the front end portion of the tube main body (100), a triangular shape with one concave side, a triangular shape with one convex side, and a quadrangular shape.

* * * * *